United States Patent [19]

Sanborn

[11] Patent Number: 4,603,127
[45] Date of Patent: Jul. 29, 1986

[54] BETA-CYANO-BETA-THIOVINYL PHOSPHORUS COMPOUNDS AS PESTICIDES

[75] Inventor: James R. Sanborn, Modesto, Calif.

[73] Assignee: Shell Oil Company, Houston, Tex.

[21] Appl. No.: 705,258

[22] Filed: Feb. 25, 1985

[51] Int. Cl.$^4$ .................. A01N 57/04; C07F 9/165
[52] U.S. Cl. ........................................ 514/112; 558/168
[58] Field of Search .................. 260/940; 514/112; 558/168 (U.S. only)

[56] References Cited

U.S. PATENT DOCUMENTS

| | | | |
|---|---|---|---|
| 3,579,614 | 5/1971 | Miller et al. | 260/940 |
| 3,775,517 | 11/1973 | Riebel et al. | 260/940 |
| 3,884,996 | 5/1975 | Lorenz et al. | 260/940 |
| 3,892,823 | 7/1975 | Maurer et al. | 260/940 |
| 3,911,055 | 10/1975 | Lorenz et al. | 260/940 |
| 3,917,751 | 11/1975 | Hoffman et al. | 260/940 |
| 3,931,358 | 1/1976 | Gutman | 260/940 |
| 4,219,511 | 8/1980 | Riebel et al. | 260/940 |

*Primary Examiner*—Anton H. Sutto

[57] ABSTRACT

Compounds of the formula

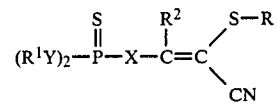

wherein each X and Y is O or S; R is alkyl, aryl or aralkyl; each $R^1$ is alkyl and $R^2$ is hydrogen, alkyl, aryl or aralkyl, are useful as pesticides.

13 Claims, No Drawings

4,603,127

BETA-CYANO-BETA-THIOVINYL PHOSPHORUS COMPOUNDS AS PESTICIDES

BACKGROUND OF THE INVENTION

Field of the Invention

This invention relates to new beta-cyano-beta-thiovinyl phosphorus compounds, their use as pesticides and to pesticidal compositions containing these new compounds.

SUMMARY OF THE INVENTION

The present invention is directed to novel compounds of formula I

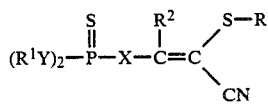

wherein each X and Y is independently O or S; R is an alkyl group containing 1 to 6 carbon atoms, optionally substituted by one or more halogen atoms of atomic number 9 to 35, an aryl or an aralkyl group containing 6 to 10 carbon atoms, optionally ring-substituted by one or more substituents selected from a halogen atom having an atomic number of 9 to 35, $NO_2$, CN, or an alkyl or alkoxy containing 1 to 4 carbon atoms optionally substituted by one or more halogen atoms; each $R^1$ is independently an alkyl group containing 1 to 4 carbon atoms; and $R^2$ is a hydrogen atom or a group as defined for R, with the proviso that $R^2$ is otherwise chosen independently of R (that is: R and $R^2$ can be alike or different substituents within their definition). The compounds are useful as pesticides, e.g. for control of insects and acarids, particularly, mites.

The compounds of formula I of the invention can exist as geometric isomers because of the presence of the carbon-carbon double bond. The present invention contemplates all pesticidally active geometric isomer forms of the compounds as well as natural and artificial mixtures thereof.

Non-limiting embodiments of the invention include: S,S-dimethyl O-beta-cyano-beta-(benzylthio)vinyl phosphorotrithioate, S,S-dibutyl O-beta-cyano-beta-(phenylthio)vinyl phosphorotrithioate, O,O-dimethyl O-beta-cyano-beta-(isobutylthio)vinyl phosphorothioate.

Because of their pesticidal properties, including their use for control of mites, various embodiments of the invention are preferred as set forth below.

In one embodiment of the invention, $R^2$ is a hydrogen atom, a methyl group or a phenyl group. Preferably, $R^2$ is a hydrogen atom.

In another embodiment of the invention, $R^1$ is a methyl or ethyl group. Preferably, $R^1$ is an ethyl group.

In another embodiment of the invention, X is O. In another embodiment of the invention, each Y is O.

In a further embodiment of the invention, R is an alkyl group containing 1 to 4 carbon atoms or a phenyl or benzyl group, each optionally substituted by one or more chlorine atoms. Preferably, R is a methyl, ethyl, isobutyl, secondary-butyl, phenyl or benzyl group. Compounds in which R is a phenyl group are of particular interest because of the pesticidal properties.

The compounds of formula I of the invention are prepared by treating a metal salt of the formula II

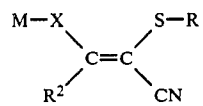

In which M is an alkali metal and X, R and $R^2$ are defined above, with a phosphorus halide

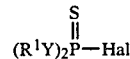

in which Y and $R^1$ are defined above and Hal is a halogen atom, preferably chlorine, in an inert solvent, such as tetrahydrofuran or acetonitrile, under basic conditions as known in the art, for example, as in Y. Nishizawa, Agric. Biol. Chem. Japan, 25, page 61 (1961).

The alkali metal salts of the formula II above are prepared by known procedures, including those of treating an appropriately substituted thioacetonitrile, $RSCH_2CN$, in which R is defined above, with an alkyl ester

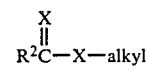

in which $R^2$ is defined above, in an inert solvent, such as tetrahydrofuran, under basic conditions, e.g. using sodium hydride or potassium tert-butoxide, for example, as in S. Kano et al., Heterocycles, 12(5), page 681 (1979).

The appropriately substituted thioacetonitriles are prepared by known procedures, such as treating chloroacetonitrile with RSNa in an inert solvent, such as ethanol, for example, as in H. J. Barker et al., Rec. Trav. Chim., 72, page 5679 (1953).

ILLUSTRATIVE EMBODIMENTS

The present invention is illustrated by the following embodiments which should not be regarded as limiting in any way. The identity of the products, including intermediates, was confirmed by elemental, infrared and nuclear magnetic resonance spectral analyses.

EMBODIMENT 1

Potassium Salt of Formyl(phenylthio)acetonitrile

In a round-bottom flask equipped with a magnetic stirrer, reflux condenser, dropping funnel and thermometer, were placed 7.5 g of (phenylthio)acetonitrile and 3.7 g of ethyl formate in 10 ml of absolute ethanol. To this mixture were added dropwise 5.6 g of potassium tert-butoxide in 50 ml of absolute ethanol. After stirring 24 hr at room temperature, the solvent was removed yielding 10.6 g of product as a white solid, which was used in the next step without further purification.

EMBODIMENT 2

O,O-Diethyl O-(2-Cyano-2-(phenylthio)ethenyl) Phosphorothioate

In a round-bottom flask equipped with a magnetic stirrer and reflux condenser under nitrogen, were placed 4.3 g of the salt of Embodiment 1 above and 3.72 g of O,O-diethyl phosphorochloridothioate in 25 ml of acetonitrile. The reaction mixture was stirred for 4 hr at room temperature. The solvent was removed and the residue was taken up in methylene chloride and washed with water. The organic layer was dried over sodium sulfate and then distilled on a Kugelrohr apparatus. The yield was 0.6 g of the desired product, boiling at 135°-140° C. (0.05 mm).

EMBODIMENTS 3-24

Following procedures similar to those described in Embodiments 1 and 2 above, other beta-cyano-beta-thiovinyl phosphorus compounds of the invention were prepared and are set forth in Table 1 below.

TABLE 1

BETA-CYANO-BETA-THIOVINYL PHOSPHORUS COMPOUNDS $$(C_2H_5O)_2\overset{\overset{S}{\|}}{P}-O-\overset{\overset{R^1}{|}}{C}=C\overset{SR}{\underset{CN}{\diagdown}}$$

| Embodiment | R | R$^1$ | Boiling Point* °C. (mm) |
|---|---|---|---|
| 3 | CH$_3$ | H | 95–100 (0.05) |
| 4 | tert-butyl | H | 105–110 |
| 5 | CH$_3$ | CH$_3$ | 105 |
| 6 | CH$_3$ | phenyl | 135–140 |
| 7 | CH$_3$ | p-Clphenyl | Not determined |
| 8 | phenyl | CH$_3$ | 135–145 (0.025) |
| 9 | benzyl | H | 160–165 (0.05) |
| 10 | tert-butyl | CH$_3$ | 140–145 (0.05) |
| 11 | benzyl | CH$_3$ | 150–155 (0.05) |
| 12 | C$_3$H$_7$ | H | 100–105 (0.05) |
| 13 | C$_2$H$_5$ | H | 100–105 (0.05) |
| 14 | C$_2$H$_5$ | CH$_3$ | 95–100 (0.05) |
| 15 | C$_3$H$_7$ | CH$_3$ | 110–115 (0.05) |
| 16 | i-C$_3$H$_7$ | H | 110–115 (0.05) |
| 17 | i-C$_3$H$_7$ | CH$_3$ | 100–105 (0.05) |
| 18 | C$_4$H$_9$ | H | 105–110 (0.05) |
| 19 | C$_4$H$_9$ | CH$_3$ | 100–105 (0.05) |
| 20 | i-C$_4$H$_9$ | H$_3$ | 110–115 (0.05) |
| 21 | i-C$_4$H$_9$ | H | 105–115 (0.05) |
| 22 | S—C$_4$H$_9$ | CH$_3$ | 115–110 (0.05) |
| 23 | S—C$_4$H$_9$ | H | 115–120 (0.05) |
| 24 | p-Clphenyl | CH$_3$ | not determined |

*Samples were distilled through a Kugelrohr apparatus.

The compounds of the invention have been found to be toxic with respect to invertebrate pests, by which is meant insects of the class Insecta and related classes of arthropods, such as the acarids (e.g., mites), ticks, spiders, wood lice and the like.

For application, a compound of the invention ordinarily is applied most effectively by formulating it with a suitable inert carrier or surface-active agent, or both. The invention, therefore, also includes compositions suitable for combatting pests, such compositions comprising an inert carrier or surface-active agent, or both, and as active ingredient at least one compound of the invention. The invention also provides a method of combatting pests at a locus, which comprises applying to that locus a compound of the invention or a pesticidal composition according to the invention.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides—i.e., horticulturally acceptable adjuvants—are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and-/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usully compounded to contain 25–75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3–7% by weight of a blend of surfactants, which act as wetting, dispersing, suspending and binding agents, and 1–3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.0001% by weight to as much as about 95% by weight of a compound of the invention as the active ingredient.

The compositions of the invention may also contain other ingredients, for example, other compounds possessing pesticidal, especially insecticidal, acaricidal or fungicidal properties, as are appropriate to the intended purpose.

The method of applying a compound of the invention to control pests comprises applying the compound, ordinarily in a composition of one of the aforementioned types, to a locus or area to be protected from the insects, such as the foliage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

EMBODIMENT A

Pesticidal Activity

Activity of compounds of the invention with respect to insect and acarine pests was determined by using standardized test methods to measure the toxicity of the compounds as follows:

I. Houseflies (*Musca domestica* (Linne)) were tested by placing 50 4- to 5-day old adult houseflies into a spray cage and spraying with 0.6 ml of a solution of test compound. After spraying, the flies were observed to ascertain any knockdown effect, and then were anesthetized with $CO_2$ and transferred to a recovery cage containing a milk pad for food. The cages were held for 18–20 hours after which mortality counts were made. Both dead and moribund flies were counted. The test were conducted employing several different dosage rates for each test compound.

II. Pea aphids (*Acyrthosiphon pisum* (Harris)) were tested by placing about 100 adult aphids on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing several different dosage rates for each test compound.

III. Adult female two-spotted spider mites (*Tetranychus urticae* (Koch)) were tested by placing 50–75 mites on the bottom side of leaves of pinto bean plants. The leaves were sprayed with dilutions of an acetone solution of the test compound in water containing an emulsifier and kept under laboratory conditions for about 20 hours, at which time mortality counts were made. The tests were conducted employing several different dosage rates for each compound.

IV. Mosquito larvae (*Anopheles albimanus* (Weide)) were tested by placing 10 living and active mosquito larvae in a jar containing a 0.1 ml aliquot of a 1% acetone solution of the test compound thoroughly mixed with 100 ml of distilled water. After 18–22 hours, mortality counts were taken. Both dead and moribund larvae were counted as dead. Larvae which did not swim after being prodded with a needle were considered moribund. The tests were conducted employing several different dosage rates for each compound.

V. Third instar corn earworm larvae (*Heliothis zea* (Boddie)) were tested by spraying broad bean plants with dilutions of an acetone solution of the test compound in water containing an emulsifier. Immediately after spraying, 5 larvae were transferred to the plant and held for 44–46 hours, at which time the dead and moribund larvae were counted. The tests were conducted employing several different dosage rates for each test compound.

In each set of tests, identical tests were conducted using Parathion as a standard for comparison.

In each instance, the toxicity of the test compound was compared to that of a standard pesticide, parathion, the relative toxicity of the test compound then being expressed in terms of the relationship between the amount of the test compound and the amount of the standard pesticide required to produce the same percentage (50%) of mortality in the test insects. By assigning the standard pesticide an arbitrary rating of 100, the toxicity of the test compound was expressed in terms of the Toxicity Index, which compares the toxicity of the test compound of the invention with that of the standard pesticide. That is to say, a test compound having a Toxicity Index of 50 would be half as active, whereas one having a Toxicity Index of 200 would be twice as active, as the standard pesticide.

VI. Corn rootworm larvae (*Diabrotica undecimpunctata undecimpunctata* (Mannerheim)).

Each test chemical was dissolved in a solvent and thoroughly incorporated into dry soil. After venting traces of solvent the soil moisture level was brought to 9.1% by adding water and thoroughly mixing.

60 g of moist soil was added to a 4 oz, wide-mouthed jar filling it ½ full. Two sweet corn seeds, which had been surface sterilized in 0.26% sodium hypochlorite solution for 15 minutes and rinsed with water, were pressed into the soil near the perimeter of the jar. A small cavity of about 2.5 cc was opened in the surface of the soil, and 20 corn rootworm eggs were placed in the wall. They were immediately covered over with fine-sieved Zonolite or Vermiculite, and the covering material was wet with about 1.5 cc of water. The jar was then capped with a lid into which two 2 mm holes had been drilled for ventilation. The jars were placed under greenhouse-type grow lamps at 27° C. for holding. The eggs were generally two to four days old.

Periodically, the jar's contents were examined for the presence of live larvae, and the number was recorded. In these tests the results were evaluated as follows:

| Rating | Control Potential | Larval Count |
| --- | --- | --- |
| 0 | Complete control | 0 |
| 1 | Excellent | >0-<3 |
| 2 | Good | >3-<6 |
| 3 | Fair | >6-<10 |
| 4 | Poor | >10 |

Results of Tests I–VI

Each compound tested was found to have activity against one or more of the pest species tested. In general, the compounds were more active against acarids, e.g. spider mite, and the Toxicity Index of the more active compounds against mites is set forth in Table 2.

TABLE 2

| Embodiment Number | Toxicity Index Spider Mite |
| --- | --- |
| 2 | 800 |
| 3 | 57 |
| 6 | 10 |
| 9 | 20 |

TABLE 2-continued

| Embodiment Number | Toxicity Index Spider Mite |
| --- | --- |
| 13 | 10 |
| 21 | 87 |
| 23 | 29 |

What is claimed is:

1. A compound of formula I

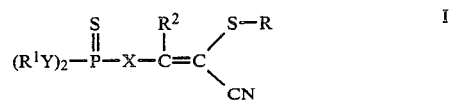

wherein each X and Y is independently O or S; R independently is an alkyl group containing 1 to 6 carbon atoms, optionally substituted by one or more halogen atoms of atomic number 9 to 35, an aryl or an aralkyl group containing 6 to 10 carbon atoms optionally ring-substituted by one or more substituents selected from a halogen atom having an atomic number of 9 to 35, $NO_2$, CN, or an alkyl or alkoxy containing 1 to 4 carbon atoms optionally substituted by one or more halogen atoms; each $R^1$ is an alkyl group containing 1 to 4 carbon atoms; and $R^2$ is a hydrogen atom or a group as defined for R, with the proviso that the substituent $R^2$ is otherwise chosen independently of R.

2. A compound according to claim 1 wherein $R^2$ is a hydrogen atom, a methyl group or a phenyl group.

3. A compound according to claim 2 wherein $R^2$ is a hydrogen atom.

4. A compound according to claim 3 wherein $R^1$ is a methyl or ethyl group.

5. A compound according to claim 4 wherein $R^1$ is an ethyl group.

6. A compound according to claim 5 wherein X is O.

7. A compound according to claim 6 wherein each Y is O.

8. A compound according to claim 7 wherein R is an alkyl group containing 1 to 4 carbon atoms or a phenyl or benzyl group, each optionally substituted by one or more chlorine atoms.

9. A compound according to claim 8 wherein R is a methyl, ethyl, isobutyl, secondary-butyl, phenyl or benzyl group.

10. A compound according to claim 9 wherein R is a phenyl group.

11. A pesticidal composition comprises a pesticidally effective amount of a compound according to claim 1 and at least one surface-active agent or carrier.

12. A method of combatting pests at a locus comprises applying to the pests or the locus a pesticidally effective amount of a compound according to claim 1.

13. A method according to claim 12 wherein the pests are acarids.

* * * * *